(12) United States Patent
Maeda et al.

(10) Patent No.: US 8,128,959 B2
(45) Date of Patent: Mar. 6, 2012

(54) POLYMERIC PHARMACEUTICAL AGENT FOR TREATMENT OF CANCER AND METHOD FOR PRODUCTION OF THE SAME

(75) Inventors: Hiroshi Maeda, Kumamoto (JP); Khaled Greish, Kumamoto (JP)

(73) Assignee: Hiroshi Maeda, Kumamoto (JP)

( * ) Notice: Subject to any disclaimer, the term of this patent is extended or adjusted under 35 U.S.C. 154(b) by 791 days.

(21) Appl. No.: 11/918,651

(22) PCT Filed: Apr. 13, 2006

(86) PCT No.: PCT/JP2006/307852
§ 371 (c)(1),
(2), (4) Date: Oct. 17, 2007

(87) PCT Pub. No.: WO2006/112361
PCT Pub. Date: Oct. 26, 2006

(65) Prior Publication Data
US 2009/0062476 A1    Mar. 5, 2009

(30) Foreign Application Priority Data
Apr. 18, 2005 (JP) ................... 2005-120159

(51) Int. Cl.
*A61K 47/48* (2006.01)
*A61K 33/30* (2006.01)
*A61K 31/555* (2006.01)
*B01F 3/00* (2006.01)

(52) U.S. Cl. ..... 424/486; 424/641; 424/643; 424/78.33; 514/185; 514/410; 514/772.6; 525/360; 525/370; 516/77

(58) Field of Classification Search .................... 516/77; 424/486, 641, 643, 78.33; 514/185, 410, 514/772.6; 525/360, 370
See application file for complete search history.

(56) References Cited

U.S. PATENT DOCUMENTS
4,182,752 A    1/1980 Maeda et al.
(Continued)

FOREIGN PATENT DOCUMENTS
EP    0 583 955    2/1994
(Continued)

OTHER PUBLICATIONS

Greish K, Sawa T, Fang J, Akaike T, Maeda H., "SMA—doxorubicin, a new polymeric micellar drug for effective targeting to solid tumours", J Control Release 2004;2:219-30 (Jun. 18, 2004), online@ http://www.sciencedirect.com/science.*

(Continued)

*Primary Examiner* — Daniel S Metzmaier
(74) *Attorney, Agent, or Firm* — Wenderoth, Lind & Ponack, L.L.P.

(57) ABSTRACT

The present invention provides a polymeric agent which can incorporate a large amount of a drug, accumulate selectively in a tumor site, and has a molecular size of more than that for renal excretion. A metalloporphyrin derivative (such as zinc protoporphyrin) is associated with a styrene-maleic acid copolymer via non-covalent bond to give a SMA micelle complex, allowing provision of a polymeric pharmaceutical agent for treatment of cancer with a large amount of the drug incorporated. The SMA micelle complex can be produced by a method, wherein the metalloporphyrin derivative reacts with the styrene-maleic acid copolymer in the absence of a condensation agent under an alkaline condition, solubilized, adjusted to have a pH of 6-8, and subjected to a procedure for separating a polymer component to recover the micelle complex component for the polymeric pharmaceutical agent.

7 Claims, 4 Drawing Sheets

U.S. PATENT DOCUMENTS

| | | | |
|---|---|---|---|
| 4,732,933 A | | 3/1988 | Maeda et al. |
| 5,093,238 A | | 3/1992 | Yamashoji et al. |
| 5,449,513 A | * | 9/1995 | Yokoyama et al. ........ 424/78.08 |
| 7,026,488 B2 | * | 4/2006 | Maeda et al. .................... 525/88 |
| 7,682,630 B2 | * | 3/2010 | Maeda et al. .................. 424/486 |
| 2004/0234495 A1 | * | 11/2004 | Maeda et al. ............. 424/78.22 |
| 2004/0234597 A1 | * | 11/2004 | Shefer et al. .................. 424/468 |
| 2008/0039436 A1 | * | 2/2008 | Patel ............................ 514/185 |

FOREIGN PATENT DOCUMENTS

| | | |
|---|---|---|
| EP | 1 421 938 | 5/2004 |
| JP | 05-097857 | 4/1993 |
| JP | 06-080671 | 3/1994 |
| JP | 07-330773 | 12/1995 |
| JP | 2002-335004 | 11/2002 |
| JP | 2003-073273 | 3/2003 |
| WO | 2004/103409 | 12/2004 |

OTHER PUBLICATIONS

Cornelus F. van Nostrum, "Polymeric micelles to deliver photosensitizers for photodynamic therapy", Advanced Drug Delivery Reviews 56 (Jan. 2004) 9-16, online @ http://www.sciencedirect.com/science/journal/0169409X.*

Ethan D. Sternberg, David Dolphin and Christian Brlickner, "Porphyrin-based Photosensitizers for Use in Photodynamic Therapy", Tetrahedron 54 (Apr. 23, 1998) 4151-4202, Online @ http://www.sciencedirect.com/science/journal/00404020.*

Maeda H, Sawa T, Konno T., "Mechanism of tumor-targeted delivery of macromolecular drugs, including the EPR effect in solid tumor and clinical overview of the prototype polymeric drug SMANCS", J Control Release 2001;74:47-61 (Jul. 6, 2001), Online @ http://www.sciencedirect.com/science/journal/01683659.*

Arun K. Iyer, Khaled Greish, Jun Fang, Ryoichi Murakami, Hiroshi Maeda, "High-loading nanosized micelles of copoly(styrene-maleic acid)—zinc protoporphyrin for targeted delivery of a potent heme oxygenase inhibitor", Biomaterials 28 (2007) 1871-1881, (available online Dec. 21, 2006), online @ http://www.sciencedirect.com/science.*

Fang J, Sawa T, Akaike T, Greish K, Maeda H., "Enhancement of chemotherapeutic response of tumor cells by a heme oxygenase inhibitor, PEGylated zinc protoporphyrin". Int J Cancer 2004; 109:1-8, (Mar. 10, 2004), Online @ http://www3.interscience.wiley.com/journal/29331/toc.*

Sahoo et al., (2002) "Pegylated zinc protoporphyrin: A water-soluble heme oxygenase inhibitor with tumor-targeting capacity", Bioconjugate Chem. 13, 1031-1038 (Sep. 2002) online @ http://pubs.acs.org/toc/bcches/13/5.*

Ionel Rosenthal et al., "Sonodynamic therapy—a review of the synergistic effects of drugs and ultrasound", Ultrasonics Sonochemistry 11 (2004) 349-363, (Available online May 20, 2004), online @ http://www.sciencedirect.com/science.*

Machine Translation of Publ. No. JP 2002-335004, published Nov. 22, 2002, Japan patent Office, Tokyo, Japan (Downloaded Jun. 17, 2010), pp. 1-18.*

O'Neil, Maryadele J. et al. The Merck Index-An Encyclopedia of Chemicals, Drugs, and Biologicals (14th Ed.-Ver 4.5). Merck Sharp & Dohme Corp., a subsidiary of Merck & Co., Inc.., Headwords = Protoporphyrin IX, Hemin; Online @ http://knovel.com/web/portal/browse/display?_EXT_KNOVEL_DISPLAY_bookid=1863&VerticalID=0 (Knovel Date: Dec 1, 2007).*

Ohse, Toshiyuki et al., "SOD Activity of Mn Porphyrin Derivatives Measured by Stopped-Flow Kinetic Analysis", Porphyrins, Japan, vol. 6, No. 3/4, Dec. 1997, pp. 137-142 (with partial English translation).

Maeda, Hiroshi, "The Enhanced Permeability and Retention (EPR) Effect in Tumor Vasculature: The Key Role of Tumor Selective Macromolecular Drug Targeting", Advan. Enzyme Regul., vol. 41, pp. 189-207, 2001.

Kimura, Masami, et al.; "Intracavitary Treatment of Malignant Ascitic Carcinomatosis with Oily Anticancer Agents in Rats", Anticancer Research, 13, pp. 1287-1292, 1993.

Australian Office Action dated Jul. 2, 2010 in Australian Application No. 2006238072, Australian Gov., IP Australia, Woden, AU.

Iwai, Ken, et al., "Use of Oily Contrast Medium for Selective Drug Targeting to Tumor: Enhanced Therapeutic Effect and X-Ray Image", Cancer Research, 44, pp. 2115-2121, May 1984.

Matsumra, Yasuhiro, et al., "A New Concept for Macromolecular Therapeutics in Cancer Chemotherapy: Mechanism of Tumoritropic Accumulation of Proteins and the Antitumor Agent Smancs", Cancer Research, 46, pp. 6387-6392, Dec. 1986.

Fang, Jun, et al., "In Vio Antitumor Activity of Pegylated Zinc Protoporphyrin: Targeted Inhibition of Heme Oxygenase in Soilid Tumor", Cancer Research, 63, pp. 3567-3574, Jul. 1, 2003.

Greish, Khaled, et al. "Copoly(styrene-maleic acid)-Pirarubicin Micelles: High Tumor-Targeting Efficiency with Little Toxicity", Bioconjugate Chemistry, vol. 16, No. 1, Jan. 1, 2005, pp. 230-236.

Notice of Reasons for Rejection dated Feb. 23, 2010 in Japanese Patent Application No. 2007-526841 (with English translation), Japan Patent Office, Tokyo, Japan.

Makoto, Yuasa, et al., "Anti-cancer Propoerties of Poly(styrene-co-maleic anhydride)-Bound Cationic Iron- and Manganese-porphyrins", Zairyo Gijyutu, (Material Technology) Japan, vol. 21, No. 1, Jan. 2003, pp. 7-12.

Supplementary European Search Report dated Feb. 25, 2009 in Application Patent No. 06731788.3 (in the English language); European Patent Office, The Hague, Netherlands.

Ohira, Toshiaki, et al., "Synthesis of iron cationic porphyrin modified with SMA and its evaluation of SOD activity and anticancer property", Polymer Preprints, Japan, vol. 49, No. 13, Sep. 8, 2000, pp. 3892-3893 (with English translation).

* cited by examiner

[Fig.1]
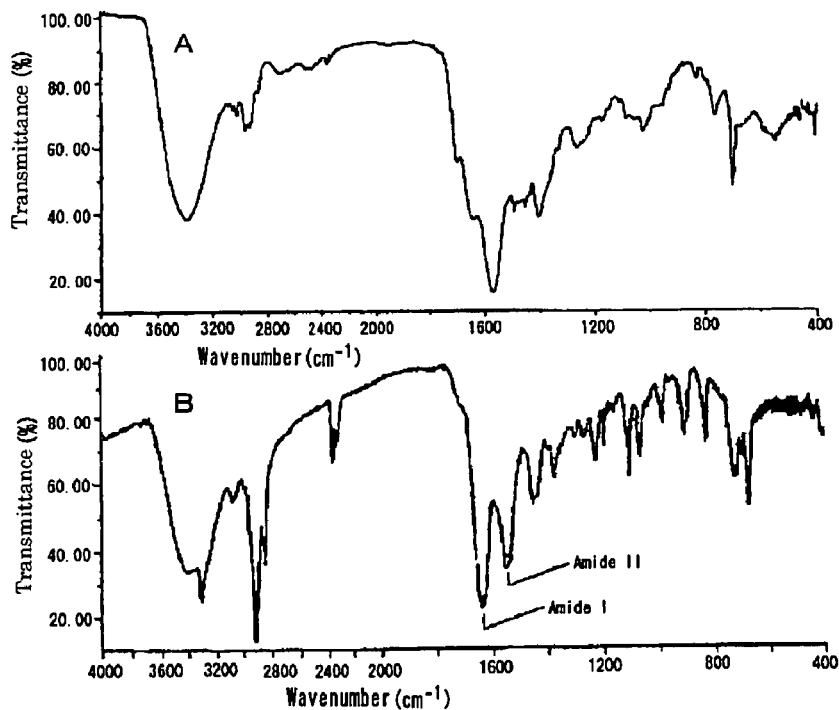
[Fig.2]
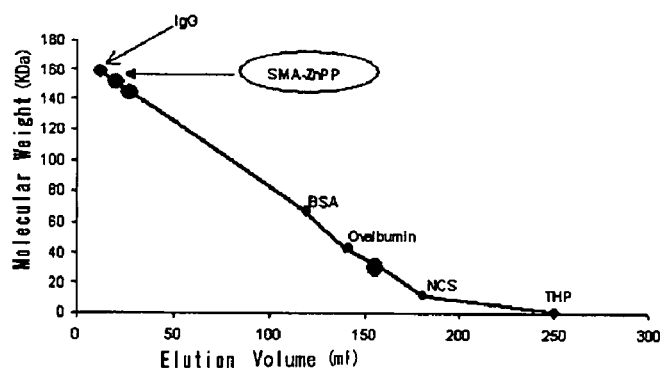

[Fig.3]
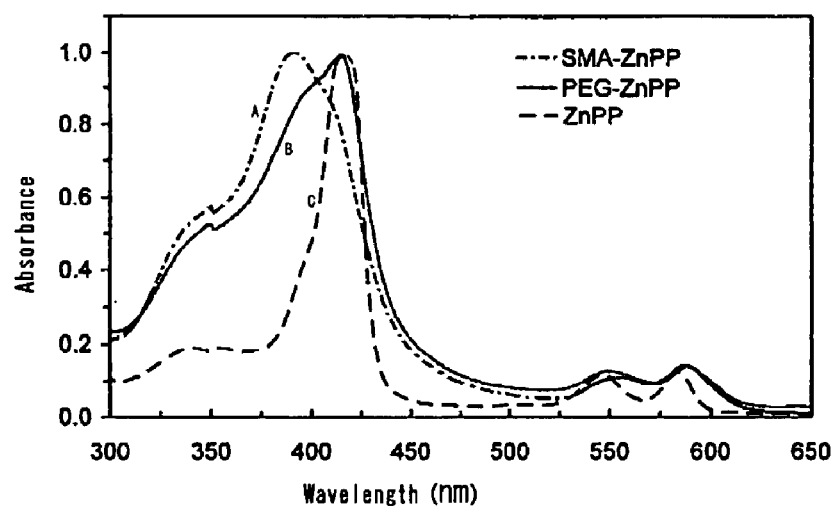
[Fig.4]
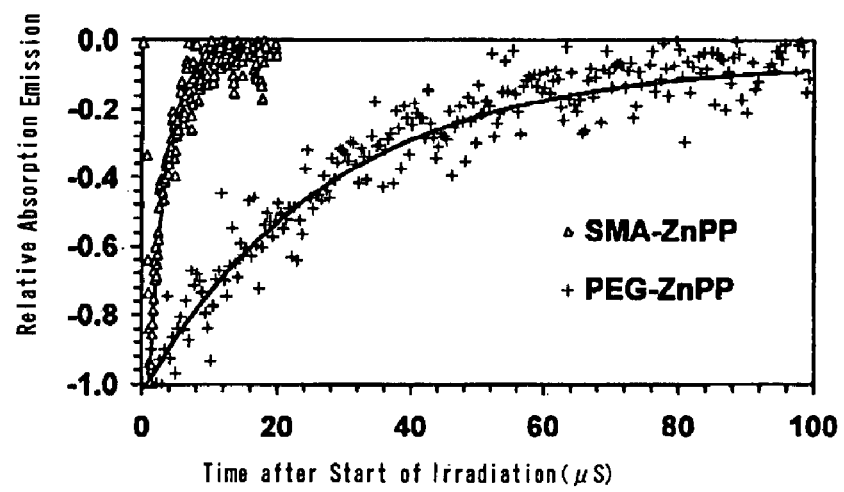

[Fig.5]
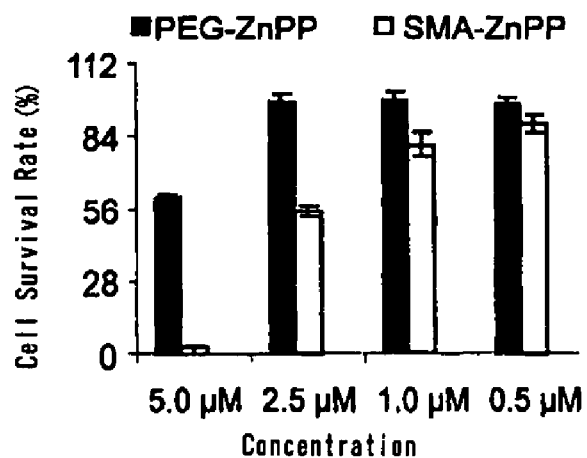
[Fig.6]
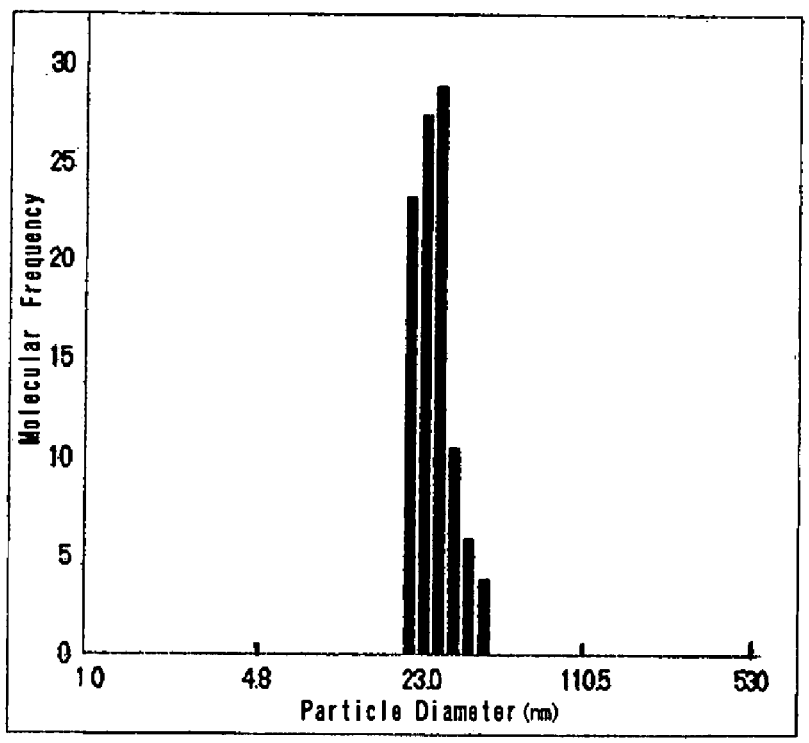

[Fig.7]
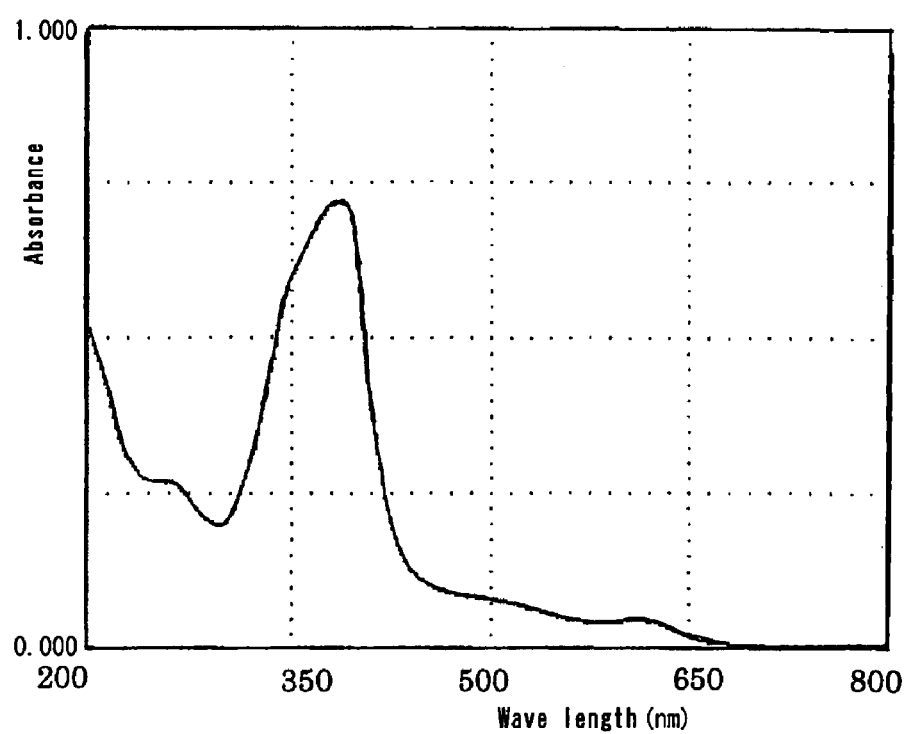

POLYMERIC PHARMACEUTICAL AGENT FOR TREATMENT OF CANCER AND METHOD FOR PRODUCTION OF THE SAME

TECHNICAL FIELD

The present invention relates to a polymeric pharmaceutical agent for treatment of cancer wherein a pharmaceutical drug for treatment of cancer is used to form a polymeric micelle complex which is selectively accumulated in lesions such as tumor regions (hereinafter designated as tumor region), is retained in the tumor regions for a longer period of time to reduce frequency of drug administration, thereby enhancing the anti-tumor effect and reducing side effects to normal organs and tissues, and also relates to an improved method for production of the same. In more detail, the present invention relates to a micelle complex wherein a metalloporphyrin (hereinafter designated as MePP) is associated with a styrene-maleic acid copolymer (hereinafter designated as SMA) to form a polymeric micelle complex having a size larger than that of a molecule that can be excreted by the kidney, a polymeric pharmaceutical agent for treatment of cancer comprising the complex as an active ingredient, and a method for producing the polymeric pharmaceutical agent for treatment of cancer wherein the aforementioned metalloporphyrin reacts directly with the SMA at a specific pH in the absence of a condensation agent to get a specific stereo-configuration.

BACKGROUND ART

In general, a drug such as an anti-cancer drug, which is administered orally or by injection, does not have the effect specific to the target lesion, and therefore, can not sufficiently exhibit the effect even if it is a potent drug, and besides, affects the normal organs and tissues other than the lesions with severe side effects. Dosage of such a potent drug is suppressed to increase due to its possibility to cause a side effect. This is the reason why the system for a lesion-oriented drug, called a drug delivery system (DDS), is continuously and competitively researched and developed worldwide. The DDS research is important especially in the field of anti-cancer drugs which have potential to bring about many side effects.

Focusing on the fact that an anti-tumor drug can be polymerized to become a lesion-oriented and sustained-release type agent, the present inventors found earlier a unique phenomenon that a polymeric agent having a molecular weight of 40 kda or more accumulates selectively in the tumor tissues and is retained there for a longer period of time, and then designated this phenomenon as an EPR (enhanced permeability and retention) effect (non-patent document 1). This phenomenon is observed in polymeric agents and lipid microparticles and the like.

Up to now, based on such observations the inventors produced many polymeric agents obtained by reacting drugs with various polymers. It was found that these polymeric agents exhibited a high rate of accumulation in tumors and inflammed lesions via the EPR effect described above, and that as the result, they became superior polymeric anti-tumor agents which were excellent in anti-tumor effect and had few side effects on normal organs as compared to low molecular weight anti-tumor drugs (Patent document 1, Patent document 2, Patent document 3 and Non-patent document 2).

Among these polymeric anti-tumor agents, the polymeric anti-tumor agent described in Patent document 3, which has a polymeric micelle complex structure formed by associating a low molecular weight anti-tumor drug with a styrene-maleic acid co-polymer (SMA) via non-covalent bonding (hereinafter designated as SMA micelle complex), has been found to be a superior anti-tumor agent that has an especially superior anti-tumor effect and also had few side effects on normal organs.

Patent document 1: Japanese Patent Publication (Kokai) No. 11-60499
Patent document 2: Japanese Patent Publication (Kokai) No. 2003-73273
Patent document 3: WO 2004/103409 A1
Non-patent document 1: Cancer Res., 44, 2115-2121, 1984; ibid, 46, 6387-92, 1986; Anticancer Res., 13, 1287-1292, 1993
Non-patent document 2: J. Controll. Release, 74, 47-61, 2001; Adv. Enzyme Regul., 41, 189-207, 2001
Non-patent document 3: Cancer Res., 63, 3567-3574, 2003
Non-patent document 4: Bioconj. Chem. 13, 1031-1038, 2002

BEST MODE FOR CARRYING OUT THE INVENTION

Meanwhile, the present inventors proposed earlier in the aforementioned patent document 2 that a metalloporphyrin derivative such as zinc-protoporphyrin represented by Formula (1) (hereinafter designated as ZnPP) which has an inhibitory activity on heme oxygenase could be conjugated with polyethylene glycol (PEG) to provide a polymeric anti-tumor agent. The metalloporphyrin derivative is an inhibitor of heme oxygenase (HO-1) which is induced in inflammation lesions and tumor lesions.

ZnPP itself is insoluble in water. In order to solubilize it in water, the present inventors have conjugated it with amphiphilic polyethylene glycol (PEG) having an average molecular weight of 100-20,000 (preferably about 5,000) (patent document 2) to create a water-soluble derivative thereof.

This PEG-ZnPP conjugate has a molecular weight of about 68,000. Thus, the in vivo behavior as a polymer is important to express the EPR effect described above.

DISCLOSURE OF THE INVENTION

Problem to be Solved by the Invention

The polymeric agent, which comprises only one molecule of ZnPP bound to PEG having a large molecular weight (in this case MW 11,000), must be administered by an amount as large as a few grams in order to supply a human with the active ingredient at a certain effective dosage or more. This means that an increased amount of the drug must be administered to a patient, and in reality, a few g to 250 g is needed to administer to attain the effective blood concentration, indicating that the protocol is impractical to perform.

Further, in Patent document 2, polyethylene glycol (PEG) was regarded as the best amphiphilic or water soluble polymer, but had to be bound to ZnPP via a diamine structure because it was difficult to conjugate directly. In the Patent document 2, in addition to PEG, SMA also was used as the polymeric compound but there was no specific disclosure. In addition, it was described that SMA also had to be reacted by dehydration condensation with an amino group-introduced on to the porphyrin to polymerize in the similar manner as seen in PEG.

Also, Patent document 3 described above, though there was no description of SMA-metal PP derivatives, disclosed a method for producing various low molecular anti-tumor drug-SMA micelle complexes, wherein a derivative of SMA such as a half-butyl ester reacts under an acidic condition in the presence of a dehydration condensation agent such as soluble carbodiimide, adjusted to have a pH of 8 or higher, then adjusted into a neutral pH zone, and subjected to separation/purification procedure for polymeric components, for example, gel chromatography such as Sephadex and an ultrafiltration membrane to recover the polymeric components.

According to this method, micelle pharmaceuticals can be produced without using a generally used micelling agent or an emulsifier (such as sugar ester, phosphatidylcholine, sphingosine, and cholesterol) that is an essential component for the liposome formulation.

However, this reaction requires a costly dehydration condensation agent such as water soluble carbodiimide. Further, when such a condensation agent was used, it was extremely difficult to remove the remaining condensation agent completely, and the complete removal could create problems such as a decrease of the drug activity, and it was difficult to put in practical use. The SMA-ZnPP micelle obtained by this method had a problem that the molecular weight was significantly smaller than the molecular weight limit for renal excretion.

Thus, the present inventors conducted research to obtain a polymeric agent which comprises SMA added to MePP to contain a large amount of the drug, and found that reaction steps are controlled to have their respective pHs to give a micelle complex of a metalloporphyrin derivative and styrene maleic acid copolymer, allowing solubilization and incorporation of the metalloporphyrin into the micelle.

This micelle complex has a polymeric micelle complex structure formed by association of a metalloporphyrin derivative and a styrene-maleic acid copolymer by non-covalent bond, and can incorporate the drug at a content as high as 10 to 60% in the micelle complex. Thus, this simple method gives a micelle a small amount of which (0.1-6 g per human) is administered to provide the efficacy.

It was found that the polymeric pharmaceutical agent for cancer treatment (hereinafter designated as SMA micelle complex) thus obtained is excellent in anti-tumor effect and has few side effects on normal organs. Here, the pharmaceutical agent for cancer treatment includes not only anti-tumor drugs that kill tumors directly but also drugs used for cancer treatment such as photosensitizers that are given before performing radiation and laser therapy, or inhibiting drugs of intracellular signal transduction.

Further, the pharmaceutical agent for cancer treatment includes agents not only for solid cancers but also for all various cancers such as lymphoma and leukemia (including adult T-cell leukemia, AIDS related T cell leukemia).

Furthermore, the inventors studied a simpler and less costly method for producing such an anti-tumor agent, and as the result found that SMA can directly react with a drug at a specifically adjusted pH in the absence of a condensation agent to produce a high purity of the agent efficiently.

In addition, this method does not need a reaction procedure for adding diaminoethane to protoporphyrin to introduce an amino group as disclosed in Patent document 2.

Means for Solving the Problem

That is, the present invention is an SMA micelle complex, wherein a metalloporphyrin derivative is associated with a styrene-maleic acid copolymer via non-covalent bond, and also a polymeric pharmaceutical agent for cancer treatment comprising the same as an active ingredient.

Also, the present invention is a method for producing the aforementioned SMA micelle complex, wherein a metalloporphyrin derivative reacts with a styrene-maleic acid copolymer in the absence of a condensation agent under an alkaline condition to get a dissolved product, which is then adjusted to have a pH of 6 to 8 and subjected to a polymeric component separation procedure (for removing a low molecular weight fraction) to recover a polymeric micelle complex component.

BRIEF EXPLANATION OF THE DRAWINGS

FIG. 1-A is an infrared absorption spectrum of SMA-ZnPP micelle complex obtained by the method of the present invention (Example 1). FIG. 1-B is an infrared absorption spectrum of PEG-ZnPP micelle complex.

FIG. 2 is a graph showing the comparison in molecular weight of SMA-ZnPP micelle complex obtained by the method of the present invention and various samples.

FIG. 3 is a UV/visible absorption spectrum of SMA-ZnPP (A), PEG-ZnPP(B) and unmodified ZnPP(C).

FIG. 4 shows the photosensitizing effect of SMA-ZnPP and PEG-ZnPP in laser flash photolysis.

FIG. 5 shows cytotoxicity of SMA-ZnPP and PEG-ZnPP under light irradiation.

FIG. 6 is a light scattering profile of SMA-hemin micelle complex.

FIG. 7 is a UV/visible absorption spectra of SMA-hemin micelle complex.

The SMA micelle complex of the present invention is a micelle complex wherein a metalloporphyrin derivative is associated with an SMA via non-covalent bonding as is quite different from what is described in Patent document 2 mentioned above, and has a greatly increased molecular weight of around 130,000, or 160,000 or above, and hence is more selectively accumulated in a tumor region and retained there for longer period of time.

Thus this is more useful as an anti-cancer agent in respect to a superior anti-tumor effect and few side effects on normal organs.

Furthermore, according to the method for production of the SMA micelle complex of the present invention, the product can be synthesized by a simple procedure from a metalloporphyrin derivative and an SMA without using a condensation agent, and the highly purified product can be obtained by a simple purification process.

BRIEF DESCRIPTION OF THE DRAWINGS

The metalloporphyrin derivative is a complex compound in which a metal coordinates with a compound having a porphyrin ring. The compound having a porphyrin ring includes protoporphyrin which is available and preferably used.

The metal to coordinate is not particularly limited so long as it is not toxic like mercury or difficult to coordinate like a univalent metal, but may be different depending on usage. When used as an anti-tumor drug, iron that does not possess a heme oxidase inhibitory activity is unsuitable, but zinc, tin, cobalt, nickel, copper and the like can be used and especially zinc is preferable. Zn-protoporphyrin (ZnPP) in which protoporphyrin coordinates with zinc are shown in following Formula (1)

[Formula 1]

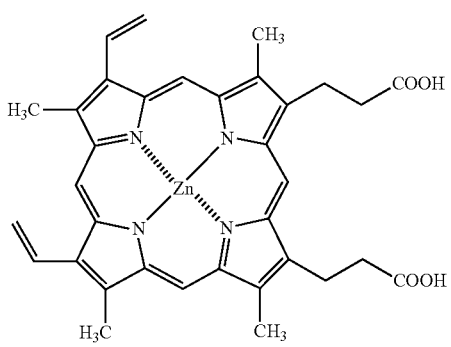

(1)

Further, a heme in which iron is coordinated, although it is unsuitable for an anti-tumor drug, can be used as a radiation sensitizer in radiation therapy. The SMA micelle comprising the heme can be administered to accumulate in a tumor site, allowing site-selective radiation therapy. Alternatively it can be used to provide a catalytic function required for generating radical molecules (R., ROO., R.). The heme that can be used includes a heme that is an iron complex of porphyrin and a hemin (hemin chloride) that is trivalent iron porphyrin coordinated with a chloride ion. Various metal PPs used as anti-tumor drugs described above such as ZnPP can also be used as radiation sensitizers.

SMA used as a polymerization agent in the present invention is obtained by co-polymerization of styrene and maleic anhydride, and is a co-polymer having the repeated units shown by following formula (2) or (3) and contains styrene and maleic anhydride as essential components.

[Formula 2]

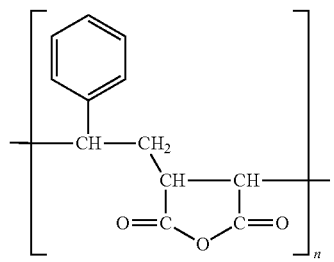

(2)

[Formula 3]

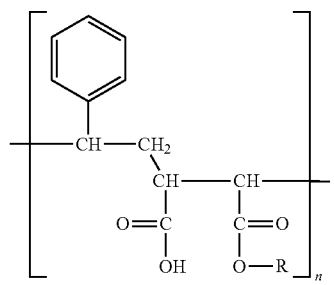

(3)

wherein R is H or a hydrocarbon, an amino acid, alcohols.

In the present invention, the SMA may be used intact as the anhydride copolymer or may be a styrene-maleic acid (or a half alkyl ester) with the completely opened ring as disclosed in Patent document 3. The anhydride copolymer is preferably used because it can be simply and easily produced without additional operations such as hydrolysis, while the styrene-maleic acid with the completely opened ring also can be preferably used because it advantageously does not need an extremely high pH (12 or above) to form the micelle in a short period of time, allowing prevention of a drug from degradation caused by strong alkalinity.

SMAs have various molecular weights depending on polymerization degree. SMA to use in the present invention as a polymerization agent has preferably a size of a trimer (about 660 Da) to about 40 kDa. More strictly, the molecular weight from 800 to 2500 is preferable because the SMA is not accumulated in the body and excreted easily out of the body.

For producing the polymeric micelle complex by the reaction of MePP and SMA, in the case of using Znpp, SMA (anhydride or hydrolysate) is mixed with ZnPP, and the mixture is supplied with an alkaline solution such as sodium carbonate to alkalize and heated under stirring. Sodium carbonate is appropriately added to maintain the alkaline condition. After all the components are solubilized, the mixture is neutralized with an acid to precipitate the micelle product. The drug is efficiently incorporated into the micelle. The mixture is further is adjusted to have a pH of neutral region to dissolve, and subjected to a separation/purification procedure of polymeric component such as ultrafiltration and column chromatography to recover the polymeric component. The procedure described above changes the stereostructure of the SMA to facilitate incorporation of the low molecular weight drug into the SMA micelle by inter-molecular interaction, and thus the micelle structure of interest is formed.

The reaction between MePP and SMA may be performed by dissolving MePP and/or SMA anhydride in an organic solvent. Compounds insoluble in water can be dissolved in the organic solvent such as tetrahydroxyfuran and dimethylsulfoxide. The solvent to use for SMA include, acetone, teterahydrofuran, dimethylformamide, dimethylsulfoxide, methyl cellosolve, acetonitrile, ethyl alcohol, and glycerin, and especially acetone and acetonitrile are preferable. The concentration in the organic solvent solution is preferably 1-30%. Here, pyridine, diaminoethane and the like may be added as a catalyst.

The reaction between MePP and SMA may be sonicated with ultrasonic waves. They can be sonicated with ultrasonic waves to form the micelle in a shorter period of time more efficiently. The condition of ultrasonication is, for example, 1 minute on and 1 minute off for 5 to 60 minutes, and it is continued at least for 5 to 10 minutes.

An ultrafiltration membrane having a cutoff molecular weight of 3,000-50,000 is preferably used to separate polymeric components. More preferably the cutoff molecular weight is 30,000-50,000. SMA-ZnPP produced by the present method has a molecular weight of 40,000 or higher. More preferably the apparent median molecular weight is 130,000-180,000.

As described above, only the materials, MePP and SMA, can be used to produce the polymeric pharmaceutical agent for treating cancer of the present invention without a subsidiary component such as a surface active agent and a dehydration condensation agent(s) needed to use. The stable micelle complex structure consisting only of SMA and MePP can be prepared by a simple procedure.

Further, as necessary, these micelles can be prepared in the presence of a stabilizer such as lactose, mannitol, amino acid, glycerin, and lecithin in an amount 1 to 100 times as much as the drug.

The polymeric micelle complex pharmaceutical agent for treating cancer of the present invention has a polymeric micelle complex structure formed by the interaction between MePP and SMA, wherein MePP is incorporated in the micelle, and the bond formed between MePP and SMA is a hydrogen, hydrophobic or ionic bond, and is not a covalent bond such as an amide or ester bond. This will be demonstrated by an infrared absorption spectrum of FIG. 1 obtained in Examples described later.

Needless to say, the micelle type SMA-MePP complex produced in this way, as seen in conventional polymeric agents, is provided with unique pharmacological characteristics compared to the original low molecular weight drugs, and also has the following superior characteristics as an agent compared to the product produced by the method of Patent document 3.

While the SMA-drug micelle complex according to the conventional method had a molecular size of 40,000 or less, the SMA micelle complex obtained by the present invention is highly polymeric to have a molecular size of as much as 100,000 or more, about 130,000-180,000, which exceeds the molecular weight of 40,000 for the renal excretion limit. This results in a big improvement in blood concentration and retention to exhibit the EPR effect. The SMA micelle complex obtained by the present invention contributes greatly to improving various anti-cancer drugs to convert to tumor-selective agents.

In addition, the micelle has a greatly increased drug content (w/w 40-60%) compared to normal liposomes (w/w 10-20%). A dehydration condensation agent such as carbodiimide, which is generally used to form a micelle, is very difficult to remove from the formed micelle, and is recognized to remain as a residual nitrogen even after 5 times purification. However, since the present invention does not use a condensation agent and a catalyst, the formed micelle is not contaminated with them, and thus is expected to be free from side effects caused by them.

Furthermore, since this product is intravenously administered to accumulate in tumor tissues via EPR effect, only the tumor tissues incorporating ZnPP can be irradiated with a same dosage of electromagnetic wave (gamma ray, x ray, ultraviolet ray, and alpha ray) to damage more by the radiation sensitizing effect of ZnPP (or other metal PP), allowing cancer therapy with a higher anti-tumor effect. That is, the polymeric pharmaceutical agent for treating cancer can be used not only as an anti-tumor agent but also as a photosensitizer.

EXAMPLE 1

Process for Producing SMA-ZnPP Micelles 200 mL of 0.1 M NaOH is added to 1.5 g of styrene/maleic anhydride copolymer having an average molecular weight of about 1,500 to bring to pH 13, and the mixture is stirred by a magnetic stirrer. While stirring, 1.5 g of finely powdered zinc (Zn)-protoporphyrin is added and continuously stirred. In the course of time, the turbid suspension becomes a dark wine-red clear solution. Insoluble ZnPP and other residues are removed by centrifugation (3,000 rpm) and the pH is lowered to around 7, and this solution is mixed with about 3 volumes of 10 mM $Na_2CO_3$/$NaHCO_3$ solution and stirred continuously. After 2 hours, the mixture is supplied with an appropriate amount of 0.1M HCl to adjust the pH to about 7, and stirred continuously for another 2 hours. Next, the solution was concentrated to 50 mL under pressure using an ultrafiltration membrane with a molecular cutoff size of 3,000 (Amicon Inc.). By this procedure free ZnPP, or non-micelled SMA or derivatives and degradation products thereof are removed. Still further, this concentrated SMA-ZnPP micelle-containing fraction is diluted with about 20 volumes of pure water, and then concentrated/washed using an ultrafiltration membrane (cutoff molecular weight 5,000) under pressure as described above. The SMA micelle of ZnPP does not leak out of this membrane and only each free low molecule component is leaked out. By this operation the micelles can be washed. The last 3 or more operations are performed using distilled water and similar operations are repeated a total of 3-5 times and then the micelles are freeze-dried to obtain powder for an injection material.

FIG. 2 shows the result of the molecular weight analysis of SMA-ZnPP using Sephadex G-150. According to this result, the molecular weight is estimated to be 130,000-150,000 which is about the same as IgG (Immunoglobulin, 160,000).

It is seen that SMA-ZnPP micelles of the present invention do not have covalent bonds between SMA and ZnPP and are associates via non-covalent bonds. To demonstrate this point, the infrared absorption spectra are shown in comparison with that of PEG-ZnPP. FIG. 1B is the infrared spectrum of PEG-ZnPP which shows an absorption of typical amide I and II of the covalent bond. On the other hand, FIG. 1-A is a spectrum of SMA-ZnPP according to the process of the present invention, and there is no absorption peak, indicating that a new bond such as the amide bond shown in FIG. 1-B is not formed.

The purified product does not pass through an ultrafiltration membrane with a cutoff molecular weight of 100,000, and the size distribution is relatively homogeneous. The UV/visible absorption spectrum is shown in FIG. 3 together with those of PEG-SnPP (FIG. 3B) and unmodified ZnPP (FIG. 3C). It is seen that when compared with PEG-ZnPP (FIG. 3B) and unmodified ZnPP (FIG. 3C), the maximum peak of absorption of SMA-ZnPP micelle complex of the present invention (FIG. 3A) is shifted to a shorter wavelength showing a small shoulder of absorption at around 350 nm.

(Treatment Efficacy)

Table 1 demonstrates the efficacy of the treatment on rabbit VX-2 tumor using the SMA-ZnPP micelle complex obtained in Example 1.

TABLE 1

Antitumor Effect of SAM-ZnPP on Rabbit VX-2 Tumor

| | | Survival rate (%) | | | |
|---|---|---|---|---|---|
| | Dose | 40 days | 60 days | 80 days | Symptoms |
| Control | Physiological saline | 0% | 0% | 0% | Solid tumor growth. Metastasis |
| SMA-ZnPP administered | 4 mg/Kg | 100% | 60% | 60% | Tumor cells enclosed. Fibrillation |
| | 8 mg/Kg | 100% | 80% | 80% | Necrosis of tumor cells. Fibrillation |
| | 12 mg/Kg | 100% | 100% | 100% | Necrosis of tumor cells. Complete Fibrillation |

Site of tumor implantation: under the liver membrane

As shown above, the SMA-ZnPP micelle complex demonstrates a strong anti-tumor effect, and the potency is superior to PEG-MePP.

(Photo Sensitization Effect by Laser Flash Photolysis)

The photosensitizing effect of SMA-ZnPP was evaluated by comparing with that of PEG-ZnPP by the flash photolysis method on Jurkat cells under normal cell culture conditions. FIG. 4 shows the relation between the time after the start of laser light irradiation (microseconds) and the relative absorption emission. The relative absorption emission represents the life span of triplet state (excitation state) of ZnPP. Concerning lifespan (half life of relative absorption emission) to compare, SMA-ZnPP has that of 2.4 μs, while PEG-ZnPP has that of 27 μs, indicating that the photosensitizing effect of SMA-ZnPP progresses efficiently at a high speed to generate singlet oxygen.

The results of FIG. 4 were obtained in Jurkat cells under the normal air atmosphere. In addition, tests were performed in water and under deoxidized condition where dissolved oxygen was removed by nitrogen gas babbling. The results are shown in Table 2. ZnPP demonstrates a more marked effect especially in Jurkat cells than in the air. Furthermore, there is little effect under a low oxygen atmosphere, suggesting that the anti-tumor effect is based on the generation of singlet oxygen by light irradiation.

(Cytotoxicity of SMA-Znpp and Peg-AnPP Under Light Irradiation)

Jurkat cells that are lymphocytes were cultured in Dulbecco's MEM medium under a 5% $CO_2$ air atmosphere at 37° C., and the survival rate of Jurkat cells was spectrophotometrically determined by MTT method 24 hours after the light irradiation. The results are shown in FIG. 5. Jurkat cells were almost all dead at a concentration of 5 μM of SMA-ZnPP micelle complex of the present invention, indicating that its effect is superior to that of PEG-ZnPP administered at the same concentration.

TABLE 2

| Sample | τt [μs] (Normal condition) | τt [μs] (after deoxidizing by $N_2$ flash for 40 minutes) |
|---|---|---|
| PEG-ZnPP in $H_2O$ | 2.5 (±0.2) μs | 406 (±40) μs |
| PEG-ZnPP in JCS | 27 (±3) μs | 325 (±30) μs |
| SMA-ZnPP in $H_2O$ | 1.4 (±0.2) μs | 484 (±11) μs |
| SMA-ZnPP in JCS | 2.4 (±0.2) μs | 92 (±40) μs 1.2 ms (±0.1) |

EXAMPLE 2

Production of SMA-Hemin Micelle 50 ml of deionized water is added to 300 mg of completely alkali-hydrolyzed SMA placed in a 200 ml beaker, and the mixture is dissolved under stirring by a magnetic stirrer, and then 0.1 M NaOH is added dropwise to adjust the pH to 10. 100 mg of Hemin (Sigma Inc.) is dissolved in 4 ml of DMSO (dimethylsulfoxide) in a 20 ml glass vial, and this solution is added dropwise in the aforementioned beaker under stirring to mix. Then, 1 M NaOH is added dropwise to lift the pH up to 12, and the mixture is stirred for 15 minutes and then supplied dropwise with 1 M HCl to bring the pH down to 2. The mixture turns to a dark brown suspension, and is stirred continuously for 30-60 minutes to dissolve. Next, the precipitates and supernatant are separated by centrifugation (3000-6000 rpm), and further 30 ml of 0.02 M acetic acid solution is added, and after stirring again (30 minutes), 0.1 M NaOH is added dropwise to this aqueous suspension of SMA-micelles to lift the pH up to 10. After stirring for 30 minutes, the pH is brought down to 7.4 again with 0.1 M HCl to obtain a dark brown, perfectly clear solution. The above operations are performed at room temperature. This solution is repeatedly concentrated and washed in the similar manner as in Example described above using an Amicon molecular sieve membrane with a cutoff molecular weight of 10 kDa, and then freeze-dried to make powder. A part of the micelles thus obtained (0.5 mg/ml) is dissolved in water, and this aqueous solution was used to obtain a light scattering profile shown in FIG. 6. From FIG. 6, it is seen that the micelles have an average diameter of 25 nm with a uniform distribution. The UV/visible absorption spectra are shown in FIG. 7. It shows a strong absorption at about 386 nm that is derived from the characteristic of the absorption of heme, weak absorption maximums at about 500 nm and 612 nm as well as a weak absorption at around 260 nm that is derived from SMA (the concentration: 0.01 mg/ml, in distilled water).

INDUSTRIAL APPLICABILITY

Many low molecular weight pharmaceutical agents for treating cancer are not selectively accumulated in tumor regions, and for that reason cause severe side effects on normal organs and tissues, even if they have a strong anti-tumor effect. Thus their dosages are limited. The micelle complex is formed between such a drug and SMA and the polymeric pharmaceutical agents for treating cancer having a molecular weight of 50,000 or more is produced to exert the EPR effect, thereby to improve the anti-tumor effect and to reduce markedly the side effects on normal organs and tissues.

The present invention makes it possible that an anti-tumor drug, ZnPP, or a radiation sensitizer, MePP such as heme protoporphyrin is associated with SMA by non-covalent bonds to form the micelle complex, allowing incorporation of a large amount of the drug into the micelle. Further, the complex, which has a molecular weight of the renal excretion limit of 40,000 or more, is greatly improved in blood concentration and blood retention, and is incorporated into cells efficiently with the EPR effect exerted, thereby to show a greater biological activity and to provide a superior efficacy as a pharmaceutical agent for treatment of cancer.

Furthermore, the present invention makes it possible that such a drug reacts with SMA to form the micelle complex at a specific pH, thereby to need neither a dehydration condensation agent nor other emulsifier that is generally difficult to remove from the complex. Thus, the method can omit the purification step to simplify the process, and can avoid the use of a dehydration condensation agent to provide a high purity product.

The invention claimed is:

1. A freeze-dried SMA-zinc protoporphyrin micelle complex comprising a zinc protoporphyrin and a styrene-maleic acid copolymer, wherein the zinc protoporphyrin and the styrene-maleic acid copolymer are non-covalently bonded.

2. A polymeric pharmaceutical agent for treatment of cancer, comprising the freeze-dried SMA-zinc protoporphyrin micelle complex according to claim 1 as an active ingredient for treatment of cancer.

3. The polymeric pharmaceutical agent according to claim 2, further comprising physiological saline.

4. A method for producing the freeze-dried SMA-zinc protoporphyrin micelle complex according to claim 1, comprising
   mixing a zinc protoporphyrin with a styrene-maleic acid copolymer in the absence of a condensation agent in an alkaline solvent to dissolve the zinc protoporphyrin and styrene-maleic acid copolymer,
   adding an acid to the resulting mixture to form a precipitate,
   adjusting the pH to 6 to 8 to dissolve the precipitate,
   subjecting to a polymeric component separation procedure to recover the SMA-zinc protoporphyrin micelle complex, and
   freeze-drying the complex.

5. The method for producing the freeze-dried SMA-zinc protoporphyrin micelle complex according to claim 4, wherein the styrene-maleic acid copolymer and/or the zinc protoporphyrin is dissolved in the alkaline solvent prior to mixing, and wherein the styrene-maleic acid copolymer and the zinc protoporphyrin react in the alkaline solvent.

6. The method for producing the freeze-dried SMA-zinc protoporphyrin micelle complex according to claim 4, further comprising an ultrasonic treatment in order to accelerate a reaction of the styrene-maleic acid copolymer and the zinc protoporphyrin in the alkaline solvent.

7. The method for producing the freeze-dried SMA-zinc protoporphyrin micelle complex according to claim 4, wherein the polymeric component separation procedure is performed by an ultrafiltration membrane for a molecular weight of 3,000 to 50,000.

* * * * *